US012765767B2

(12) United States Patent
Betensky et al.

(10) Patent No.: US 12,765,767 B2
(45) Date of Patent: Oct. 20, 2026

(54) METHOD AND APPARATUS FOR DETERMINATION OF PUPIL FUNCTION FOR A DOUBLE PASS OPTICAL SYSTEM WHEREBY THE IMAGE SURFACE IS DIFFUSIVE

(71) Applicants: Ellis Israel Betensky, Halifax (CA); Daniel Jeremy Betensky, Providence, RI (US)

(72) Inventors: Ellis Israel Betensky, Halifax (CA); Daniel Jeremy Betensky, Providence, RI (US)

(*) Notice: Subject to any disclaimer, the term of this patent is extended or adjusted under 35 U.S.C. 154(b) by 799 days.

(21) Appl. No.: 18/057,205

(22) Filed: Nov. 19, 2022

(65) Prior Publication Data

US 2023/0181031 A1 Jun. 15, 2023

Related U.S. Application Data

(60) Provisional application No. 63/283,442, filed on Nov. 27, 2021.

(51) Int. Cl.

| | |
|---|---|
| ***A61B 3/103*** | (2006.01) |
| ***A61B 3/00*** | (2006.01) |
| ***A61B 3/12*** | (2006.01) |
| ***A61B 3/15*** | (2006.01) |
| *A61B 3/10* | (2006.01) |

(52) U.S. Cl.

CPC ............ *A61B 3/103* (2013.01); *A61B 3/0008* (2013.01); *A61B 3/12* (2013.01); *A61B 3/156* (2013.01); *A61B 3/1015* (2013.01)

(58) Field of Classification Search

CPC ......... A61B 3/103; A61B 3/0008; A61B 3/12; A61B 3/156; A61B 3/1015; A61B 3/14

USPC .......................................................... 351/207

See application file for complete search history.

(56) References Cited

U.S. PATENT DOCUMENTS

2011/0095210 A1* 4/2011 Hwang .................... G01D 5/30 250/578.1

2014/0139804 A1* 5/2014 Ehrmann ............. A61B 3/0008 351/205

(Continued)

OTHER PUBLICATIONS

Li et al. , CN 113686551, A Portable Image Intensifier Resolution Measuring Device And Measuring Method (Year: 2021).*

(Continued)

*Primary Examiner* — Bumsuk Won
*Assistant Examiner* — Rahman Abdur

(57) ABSTRACT

An apparatus for determining the refractive characteristics of an imaging system having an inaccessible and diffusive image surface, such as the human eye. Refractive characteristics of the entire wavefront are ascertained by measuring the refractive power of a representative sample of segments of the pupil. By illuminating only a selected segment, the characteristics of each individual segment may be accurately measured using illumination reflected by the diffusive image surface of the subject optical system, and transmitted only through the transmitting segment. Combination of the refractive characteristics of measured segments constitutes the pupil function of the measured optical system, and can be used for a precise determination of corrective lenses. Characteristics of the system measured, including spectral sensitivity and focusing, are also determined.

1 Claim, 11 Drawing Sheets

(56) References Cited

U.S. PATENT DOCUMENTS

| | | | | |
|---|---|---|---|---|
| 2017/0299783 | A1* | 10/2017 | Schnitzler ............ | G02B 21/025 |
| 2021/0212601 | A1* | 7/2021 | Neal .................... | A61B 3/1025 |

OTHER PUBLICATIONS

Nanbara Takahiro, JP 2013048808; Fundus Photographing Apparatus (Year: 2013).*

* cited by examiner

METHOD AND APPARATUS FOR DETERMINATION OF PUPIL FUNCTION FOR A DOUBLE PASS OPTICAL SYSTEM WHEREBY THE IMAGE SURFACE IS DIFFUSIVE

CROSS-REFERENCE TO RELATED PROVISIONAL APPLICATION

This application claims the benefit of U.S. Provisional Application No. 63/283,442, filed on Nov. 27, 2021, which is hereby incorporated by reference.

BACKGROUND OF THE INVENTION

Corrective lenses for visual deficiencies of the refractive power of the eye are commonly used. However, for many people, specifically older adults, these lenses do not fully correct for the experienced deficiencies due to inaccuracies calculating an exact prescription. Problems with night vision and driving an automobile are frequent. This need for improved vision is well established. Additionally, the number of pixels available for electronic display has increased significantly, which presents new opportunities for viewing minute details. To improve the quality of corrective optics, it is necessary to precisely determine the entire wavefront, typically expressed as wavefront deviations or optical path differences, at the exit pupil for a give object point. This description is commonly known as the pupil function. The pupil function can be determined by dividing the pupil into segments, determining the optical power of those individual segments, and then combining those values mathematically. The pupil function can then be used to enable the characterization of the entire image wavefront, from which MTF or any other quality value can be computed. MTF and other subsequent calculations enable the specification of appropriate corrective lenses in an objective manner because it deals purely with calculable measurements rather than subjective perceptions.

While there are several advanced devices to measure the refractive characteristics of an optical system having an inaccessible image, including the human eye, those devices are double pass systems in which light reflects off the image, or retina and diffuses prior to reaching the device, so those systems are unable to account for irregularities of the eye. Also, most therapeutic lenses continue to be specified according to tests where an individual is asked to identify high contrast objects, usually for a single pupil diameter or object distance; often the Snellen Chart, or one similar, is employed for this task. However, this is a subjective test because it depends on the user's judgements, meaning numerous prescriptions can be identified in numerous examinations for the same individual. Typically, these subjective tests measure a first approximation to the optical power of the eye, expressed as diopters of spherical and cylindrical optical power.

Most optical systems provide an image that is accessible by viewing through a lens. However, there are some optical systems through which a third party is unable to look and in which the image must be observed through the optical system itself, thus making it inaccessible for measurement. These are referred to as double pass systems. The eye is one such system: because the retina itself is composed of different cell layers, many of which reflect both specularly and diffusely, the wavefront at the exit pupil of the eye is not set when the image is formed, but rather continues to be modified by the observing system. Furthermore, the eye itself is neither homogeneous, nor solid, so wavefronts for forming and viewing the image are not necessarily the same. As a result, ordinary image quality tests cannot be relied on to describe the images obtained from the retina or other double pass systems. Therefore, the common practice is for vision to be tested under varying conditions from which an assessment from visual acuity is subjectively determined. There are other double pass systems which use reflected light from the retina to calculate refraction, but the light paths to and from the retina are different because irregularities in the surface of the eye make it so the ray enters one part of the pupil but leaves through another. To account for this, these systems must take an average of different refractive properties, leading to imprecise aggregate refraction measurements.

PRIOR ART

There are many patents describing devices for the purpose of measuring the refractive characteristics of the human eye, but none for any double pass optical system containing a diffusive image surface. U.S. Pat. No. 7,255,442 B2 describes a device which particularly addressed the problem of stray illumination. It includes a filtering device to reduce the size of the pupil but does not disclose any means of restricting illumination to only one segment of the pupil. U.S. Pat. No. 9,192,296 B2 describes a system having separate testing and sighting optical systems: a Hartman-Shack wavefront analyzer is described wherein the individual lenslets have short focal lengths to permit measurement of large aberrations and a provision for combining lenslets is described wherein only selected lenslets receive illumination from the retinal image. The limitations of the Hartman-Shack wavefront measuring device are also minimized by lenslet spacing and focal length. The entire pupil of the eye is filled by the illumination system, however, which provides undesirable stray light. Additionally, the natural movement of the human pupil is unaccounted for and requires unnecessary movement in the device to correct. U.S. Pat. No. 10,201,276 B2 describes a system for measuring the aberration of the eye in which a variable focal length lens is used to provide focusing under varying conditions of the eye. However, the entire pupil of the eye is illuminated, thus generating undesirable stray light. U.S. Pat. No. 9,668,651 B2 describes a system for obtaining refractive measurement of the eye objectively and subjectively. While it provides a focusing motion for refractive measurement using an angular target, it does not show segmentation of the pupil to improve measurement accuracy. U.S. Pat. No. 9,572,486 describes a system to provide objective refractometry. A separate focusing system determines accommodation, but, again, there is no segmentation of the pupil, nor is the pupil function measured directly. Furthermore, the prior art all pertains specifically to the measurement of refractive errors in the eye rather than measurements of refraction in any double pass system.

DESCRIPTION OF THE INVENTION

The two primary difficulties presented when observing an image formed by a double pass optical system that contains a diffusive image surface (such as the retina) are specular reflection and general scattering. If the pupil is divided into segments, each of which is represented by a center ray, then when transmitting through a segment onto the image surface and viewing through the same segment, the refraction of that center ray will be identical to the center ray viewing the image via the optical system. The issue of specular reflection is solved because the angles for forming and viewing the image are not opposite, as indicated by the well-known requirement that the angle of incidence is equal to the angle of reflection.

Figure 1:
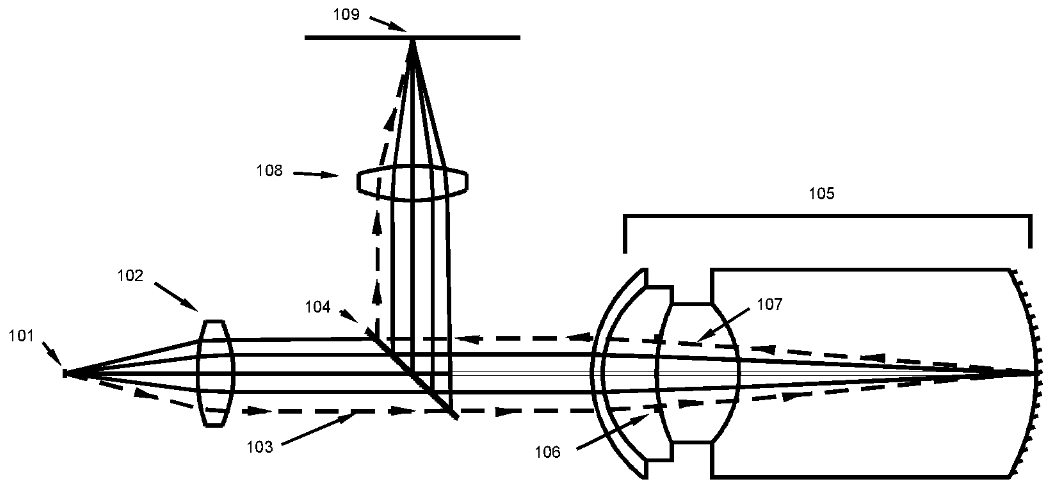
FIG. 1 shows a conventional dual path system whereby rays entering and exiting the pupil have different paths.

FIG. 1 shows a typical concept exemplified by existing devices. A light source (101) is collimated by an objective lens (102). The collimated light rays, (103), pass through a beam splitting device (104) to the pupil (106) of the eye (105) and through the eye lens (107) on to the retina. By selectively restricting some of the rays, only a portion of the pupil may be illuminated as indicated by the dashed rays (106), although all of rays may be imaged at the retina at the back of the eye where they are specularly reflected and pass a second time through the lens of the eye (107), and through the pupil (106), and on to the beam splitting device (104), where they now are directed to an imaging lens (108), which focuses the light on to a sensor (109). Because the light rays reflected by the retina pass through a different portion of the lens, even when only a small segment of the pupil is illuminated, as shown by the dashed rays, only if the eye is perfectly symmetrical about an axis, would such measurements be accurate. It is well-known that the human eye is not symmetrical as evidenced by astigmatism.

Figure 2:
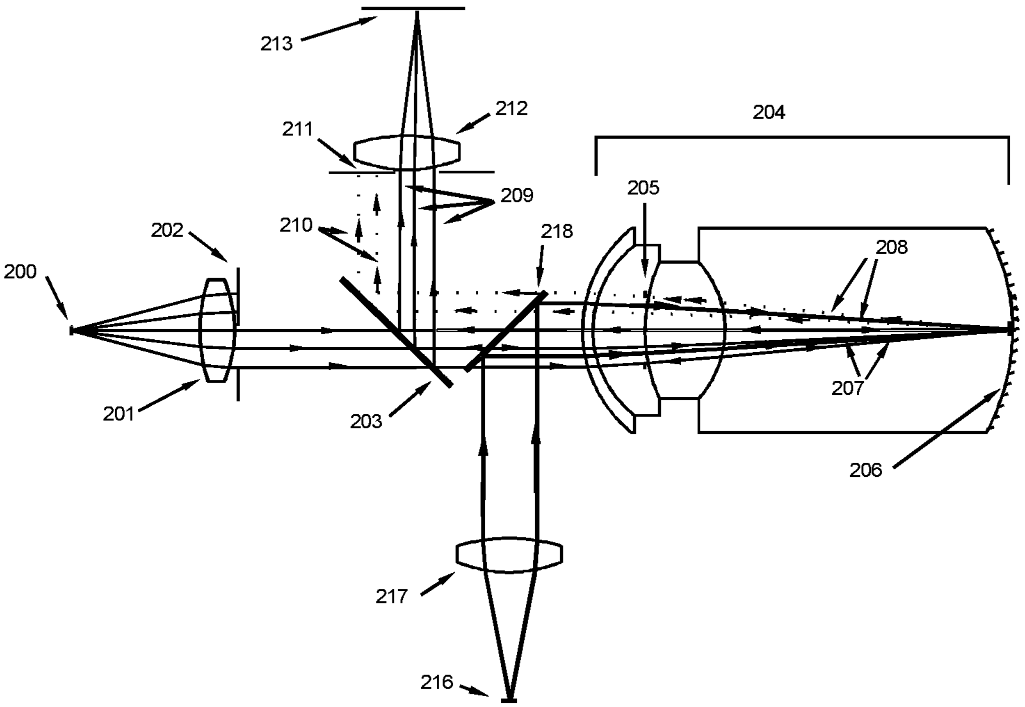
FIG. 2 shows the invention as applied to human eye measurement whereby rays entering and exiting the pupil are selectively blocked to provide a single path through the eye.

The concept of the invention as applied to human eye is illustrated in FIG. 2. A light source (200) is collimated by a lens (201), however, a device (202), which can be mechanical or optical, is used to block the illumination for one or more segment. The illumination that is not blocked passes through a beam-splitter (203), on to the eye (204), and to the pupil (205), where the selected rays pass to the retina 206), where some are reflected diffusely, (207), and others specularly, (208). Both sets of rays then transmit through the pupil to the beam-splitter (203. The rays (208) are transmitted through a second selective device (211, and focused by a lens (212), onto a sensor (213). The rays that reflected diffusely (208) are blocked by the device (211).

A second illuminating source (216) is used for sighting and providing a change of accommodation. This source can be focused by the lens (217) to present different virtual object positions to the eye, and it can be composed of various shapes and colors because a beamsplitter (218) selectively restricts light from the source (216) so as to not be received by the sensor (213).

Figure 3:
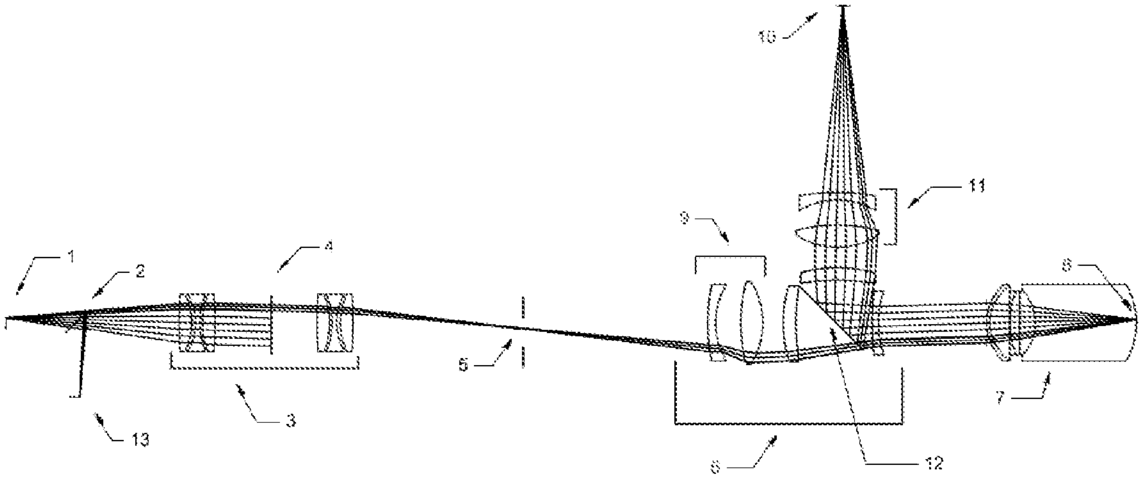
FIG. 3 shows the invention including a beam splitter providing a virtual object for varying accommodation.

In its most basic embodiment, applicable to any double pass optical system containing a diffusive image surface, movement of only one lens group is required to determine the refractive power of each pupil segment. Referring to FIG. 3, a source (1) illuminates the entire relay lens (3), but the aperture stop (4) blocks all of the illumination except for the selected segment or segments. Light from that segment of the pupil then forms an image (5), at any designated place in the retina, not just the center of the fovea, which is then re-imaged by a focusing objective (6) at the optical system's diffusive surface. Light entering the pupil will scatter and reflect in various directions. However, as shown in FIG. 3, only those rays passing through the same open pupil segment transmitted by the object source rays can pass to the image sensor (13) which follows a beam-splitter (2) placed on the optical axis and used for any open segments of the pupil. All other rays, both reflected and scattered will be blocked. Additionally, a field stop placed at the intermediate image (5) would block rays that might reach any other portion of the light sensing component of the system not included in the ones being used to form the image. The object source (1) can be an imaging device such as an LED or other equivalent monochromatic source, including a point source which must emit at a sufficient numerical aperture to illuminate the entire aperture stop. The relay lens (3) provides an accessible aperture stop which is able to be segmented. There are many types of relay lenses which satisfy this requirement. One such optical design which can be manufactured inexpensively is a symmetrical system having a center aperture stop and consisting of two halves, one on each side of the aperture stop (4). The segmented aperture stop must block illumination selectively, which can be accomplished by using light valves such as LCD devices or segmented mirrors using a reflex relay.

Light from the object source transmitting through any segment and focused at (5) is reimaged by the double pass optical system under test. In the absence of defects concerning the lens of the system (such as myopia, hyperopia, presbyopia or astigmatism for the eye), an image will be formed at the optical system's diffusive surface. When the image is not formed at the diffusive surface, the moving lens group (9), part of the focusing objective (6), is moved from its nominal position and reimages the particular segment image at (5) to a virtual distance that will be focused by the system at the sensor. Because the segmented aperture stop is conjugate to the pupil, only the corresponding segment of the pupil will be illuminated. The optical design of the focusing objective (6) can have many forms. However, it must be well corrected for all pupil segments and also must image the aperture stop (4) accurately into the pupil. It can compensate for significant refractive errors, limited only by the complexity of the optical system and its manufacturing cost. The image formed at the sensor is imaged by the relay lens back toward the source, but that image path is intercepted by a beam splitter near an image sensor (2). This image sensor determines the best-focus of the focusing objective. A measure of an appropriate metric, such as point spread function can be transmitted to a focus control mechanism which then directs the focus group to move appropriately. This moving portion comprises few lens elements, whose motion is within conventional camera lens focusing technology. To increase the extent of focusing, greater complexity of the optical components and associated movements may be necessary. The movement of the lens unit (9) is calibrated according to a corresponding deviation from the position of a perfect system.

In a second configuration intended to measure the optical characteristics of an eye, a provision for sighting and testing for different accommodations may be desired, and, therefore, a second beam splitter (12) can be provided so that a sighting source (10) can be viewed by the subject. The beam splitter can be a dichroic mirror so that light projected into the system will be a different wavelength than that which is emitted by the object source. By moving a lens group (11) the sighting system provides an image at set distances from the eye, and thus allows the subject to accommodate the eye under test. The illuminated test object viewed by the subject, and formed at the retina can have different shapes and durations during the test because it is not imaged on the sensor and has a wavelength of light that is not passed by the dichroic beam splitter (12). If the sighting source is programmable, such as an LED, various types of moving targets can be used to prevent movement during the few seconds required to measure the pupil function for any accommodation distance. The programmable sighting source allows the subject to focus on a specific image, which significantly reduces the natural darting motion of the eye and enables refractive power to be calculated accurately. The whole eye views the LED sighting source, which differs from the LED object source that a single pupil segment views. Additionally, monochromatic filters must be used in the optical system of the object source, so that none of the light from the sighting source is seen by the object sensor. By using two different colors of light, monochromatic filters could eliminate any stray light entering the object source from the sighting source. In this way, the eye can be distracted by whatever image, movement or color the LED sighting source is programmed for, but this light never reaches the focus sensor of the object source because it is filtered out prior to its arrival.

Additionally, by using LEDs, the color of the object source could be modified to measure the refractive power of the eye having been exposed to different wavelengths of light. Furthermore, a programmable sighting source would allow the accommodation of the eye to be measured under different stimuli. This would be a valuable source of research to help determine the relation between refractive errors in response to different wavelengths of light and various ophthalmological diseases such as keratoconus or retinitis pigmentosa. The LED object source can also be aimed to image at various off-axis positions to provide a different angle which enables us to inspect different spots on the retina. This would provide for the comparison with respect to color and surface texture of specific locations on the retina. From these data, we could possibly detect the presence of eye related disease such as macular degeneration and retinitis pigmentosa at an early stage.

The device disclosed measures the pupil function expressed in wavefront deviations. The pupil function can be measured for different pupil openings, particularly important concerning large aberrations and for determining acuity for night vision. Also, asymmetries of a double pass optical system, and line of sight deviations can be determined using conventional computational methods of analysis and interpolation. In addition, conventional optical design software can use the pupil function for optimization of any lens to be added or inserted into the system, such as custom contact lenses for the eye. Aberrated objects and aspherical correcting lenses are well known.

Figure 4:
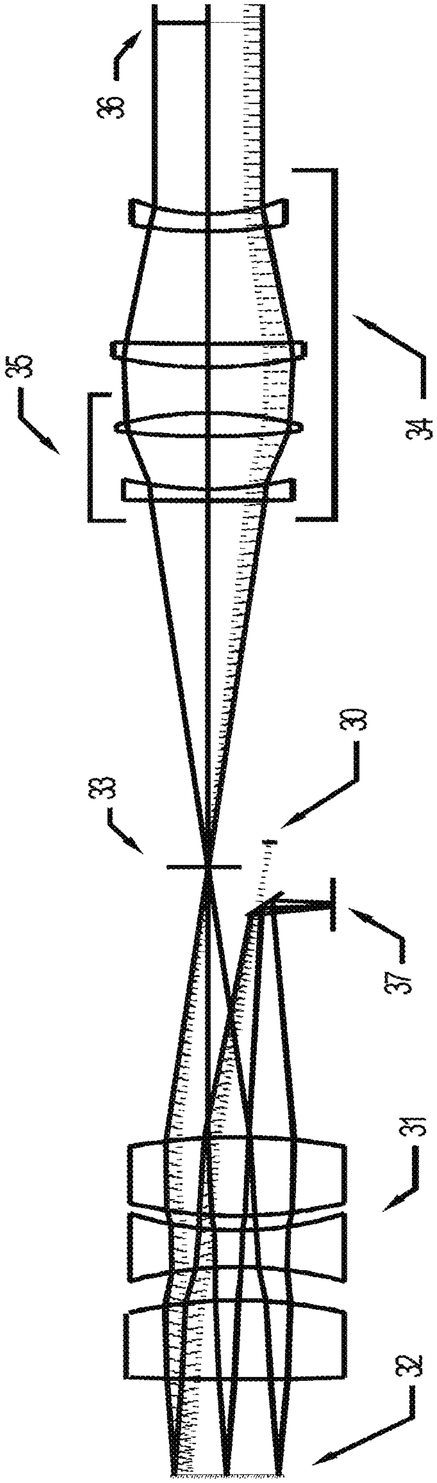
FIG. 4 shows an object source imaged by a reflex relay system whereby adjustable mirrors are placed at the stop so as to illuminate selected segments of the pupil.

A third embodiment, also meant for the eye, is shown in FIG. 4. The object source (30) illuminates the entrance pupil of a relay lens (31) having an accessible aperture stop (32). The relay lens in this embodiment is reflex from where a mirror is placed at the aperture stop and reflects the light back to its origin. To separate the object and image, the object is typically placed a suitable distance from the optical axis. The light valve can be placed in front of the mirror, or the mirror itself can be segmented. A digital micro mirror (DMD) is an example of a segmented mirror used as a light valve. In the configuration of FIG. 4, the object source has a finite size rather than a point; thus, a field stop at (33) can limit the size of the image on the retina observed. A solid pencil of light from a point on the object source is shown traversing the system to the pupil where it will then be imaged at the retina. The image (33) is then re-imaged by a focusing objective (34) into the pupil of the eye (36) where it is focused by the optical system of the eye onto the retina. An image of the retinal image is then formed and transmitted in reverse according to the same pencil of light shown through a beam-splitter onto the sensor (37).

Figure 5:
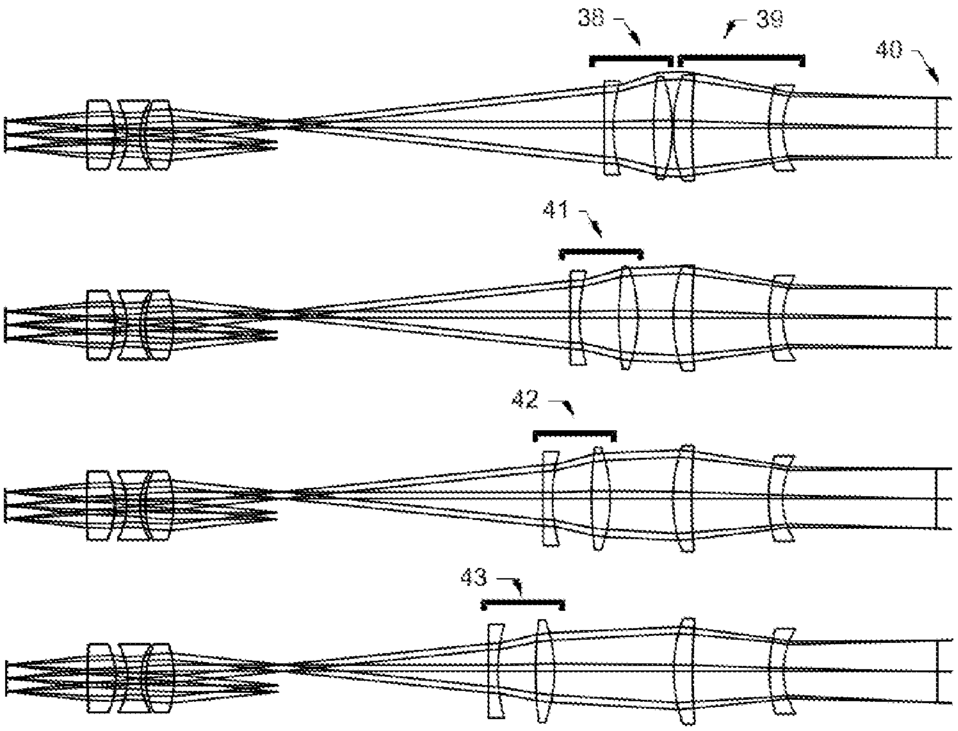
FIG. 5 shows a focusing lens used to measure variations in optical power for various pupil segments.
Figure 6A:
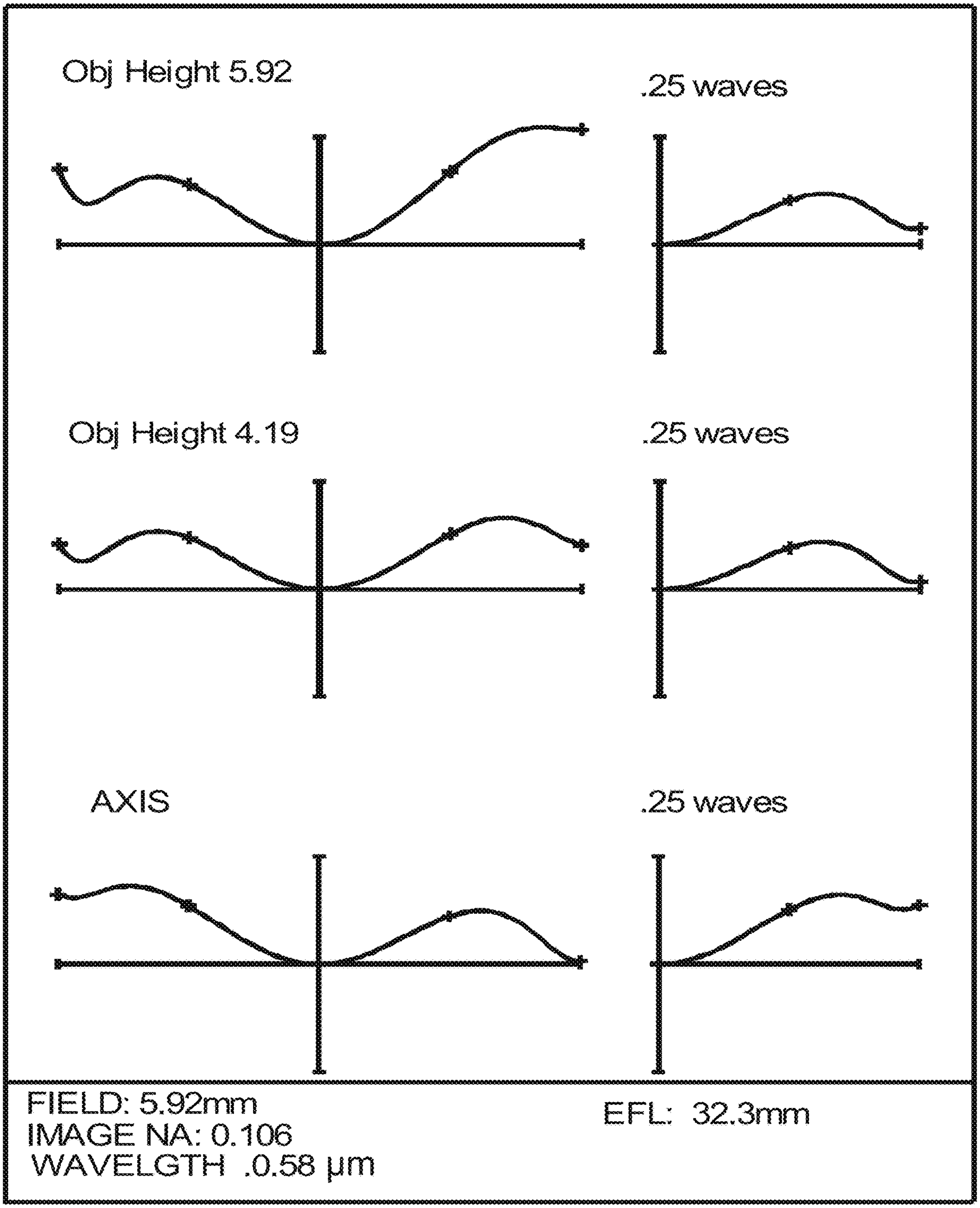
FIG. 6*a*-*d* show wave front aberrations in a conventional format, plotted across the pupil for both x and y azimuths at varying object distances.
Figure 6B:
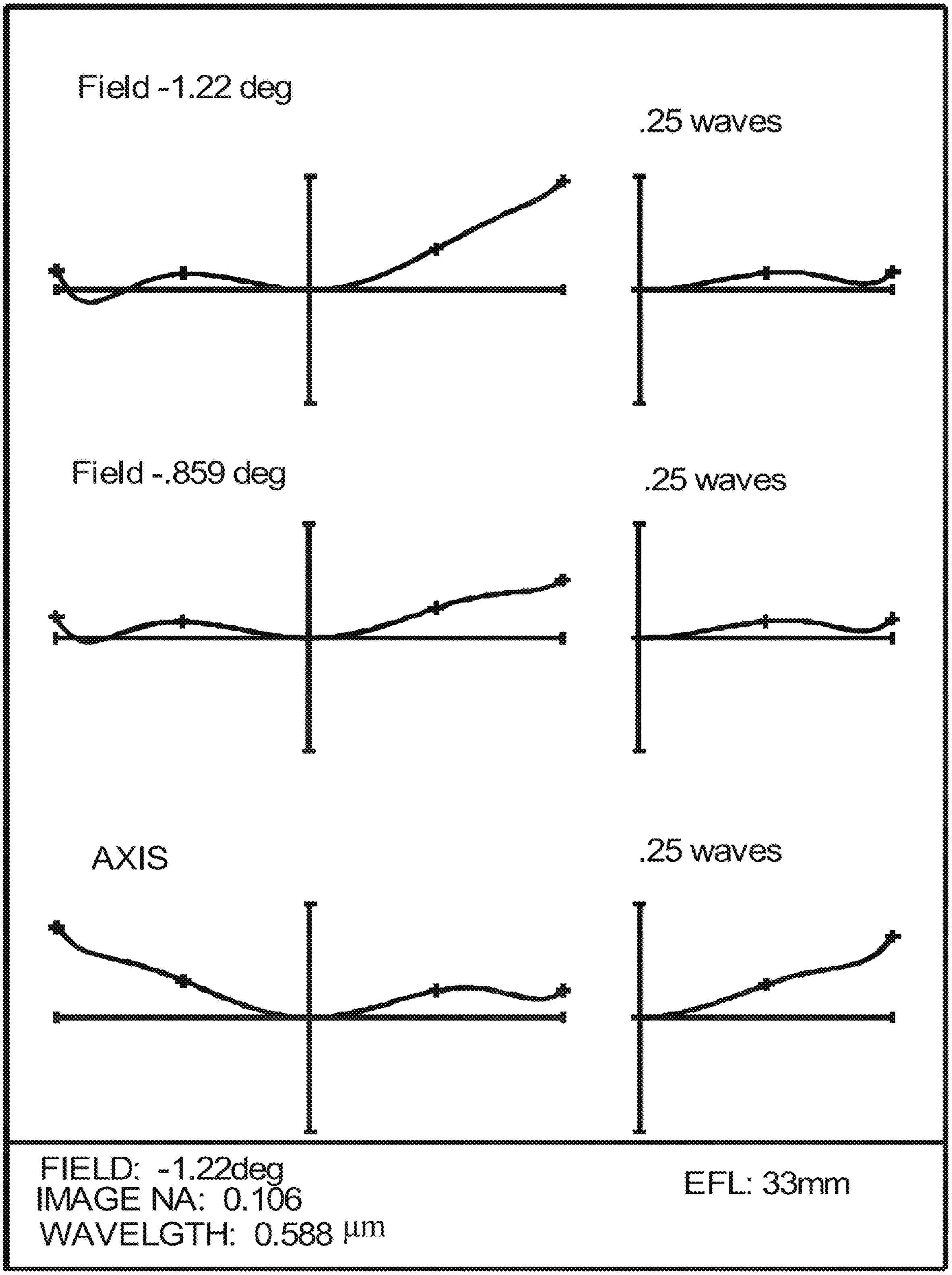
Figure 6C:
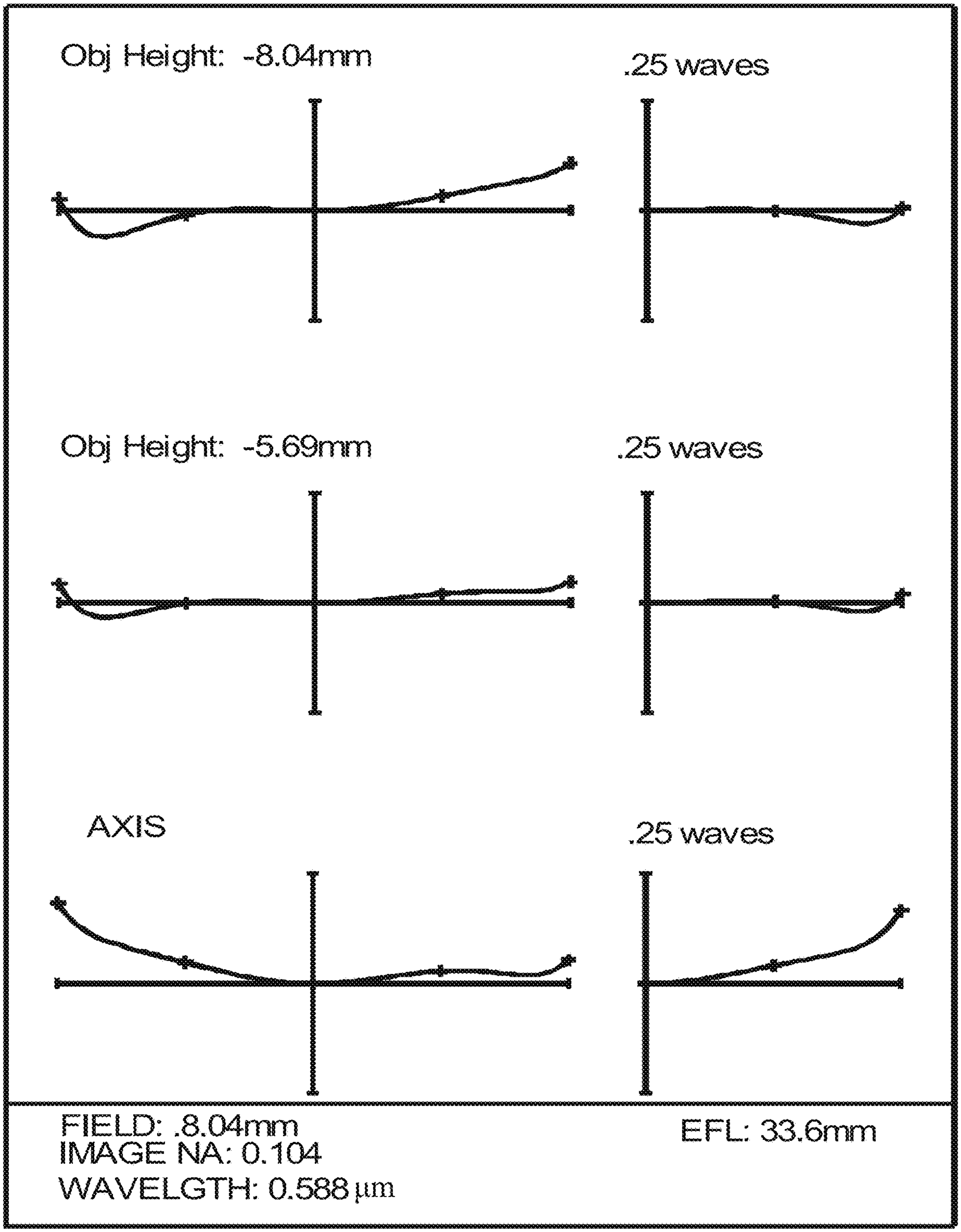
Figure 6D:
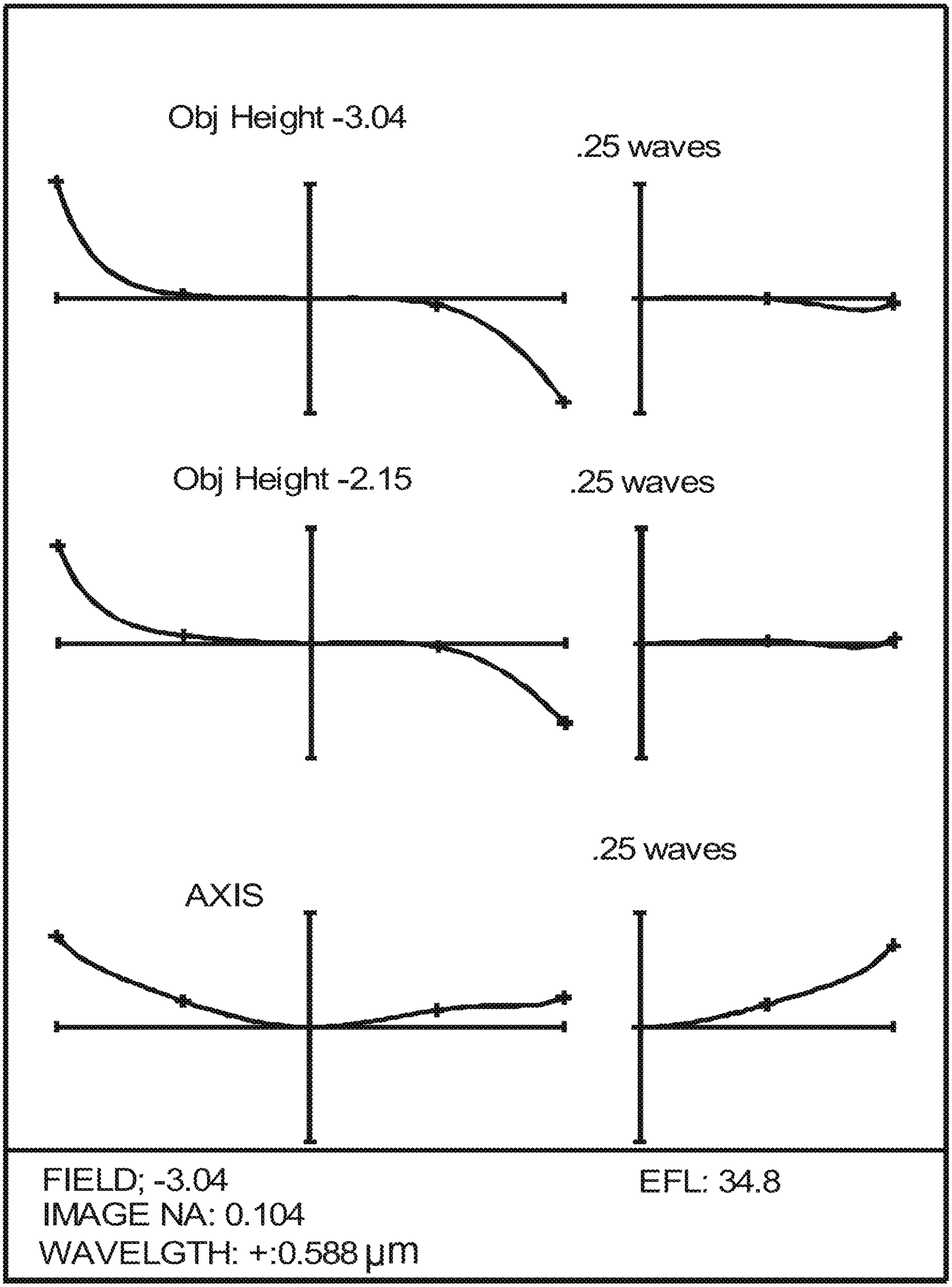

A further embodiment to be used with the eye is shown in FIG. 5. A fixed lens group (39) is positioned nearest the pupil of the eye (40), while a single group, moves to provide for a variable refracting power to compensate for the refractive deviations of the light pencil for any particular segment of the pupil. The moving group is positioned at (38) for object distances of −275, (41) for infinity, (42) for 385 and (43) for 137 mm. This example illustrates a multi-configuration system that provides fixed entrance and exit pupil positions, and magnification for any object distance. One with skill in the art of multi-configuration optical design could choose other systems to achieve the desired result. The example shown in FIG. 5 is very compact and comprises only seven lens elements, a small beam-splitter, a LCD light valve, an image sensor, and one electronically controlled moving lens group, which can be produced at low cost. The length of the system from the pupil of the eye is less than 100 mm. If the extra cost and size of the sighting system shown in FIG. 3 is not desired, the subject can view a wall chart or other target. In this embodiment the device can be used for rapid object screening. The optical system shown in FIG. 5 is capable of presenting a nearly perfect image of the object source into the entire fully opened pupil of the eye. However, in general use only a small subset of the pupil would be illuminated.

The device described herein can be used to measure the pupil function of a fully opened pupil, and because measured wavefront data are not functionally instrument dependent, conventional optical design software can be used to add or replace components as needed to improve vision. FIGS. 6A through 6D show the wavefront aberrations for each focus position: A (−275 mm), B (infinity), C (385 mm) and D (137 mm) computed for the entire pupil. It can be seen that the uncorrected aberration is less than ¼ for any one segment and would be sufficient to provide essentially perfect imaging.

EXAMPLES

Optical design prescription data for the focusing objective are given in Table 1. Conventional optical design terminology is used. Each configuration represents a different focal length, object or image position.

In Table 2, the optical design prescription data are given for a symmetrical relay lens. If a reflex-type is desired, then only those lens elements on one side of the aperture stop are needed and the aperture stop surface is a mirror.

The design is limited only by chromatic aberrations which can be reduced upon the selection of the illumination wavelengths to be used in the system. There are many types of 1:1 lenses that can include an accessible segmented aperture stop, and, when designed correctly, satisfy the requirements of the invention.

Figure 7:
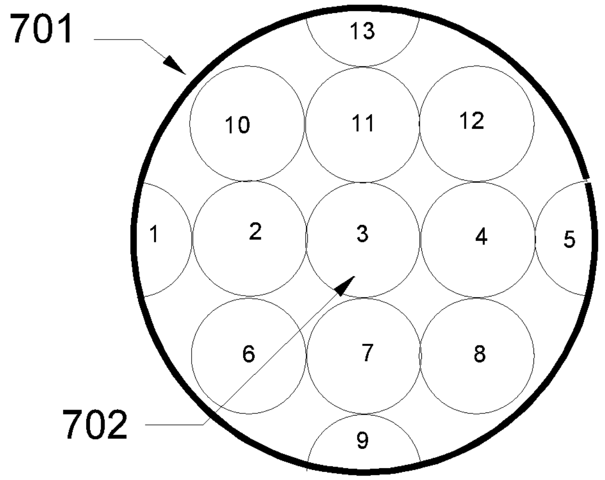
FIG. 7 shows a pupil divided into 12 segments for evaluation.
Figure 8:
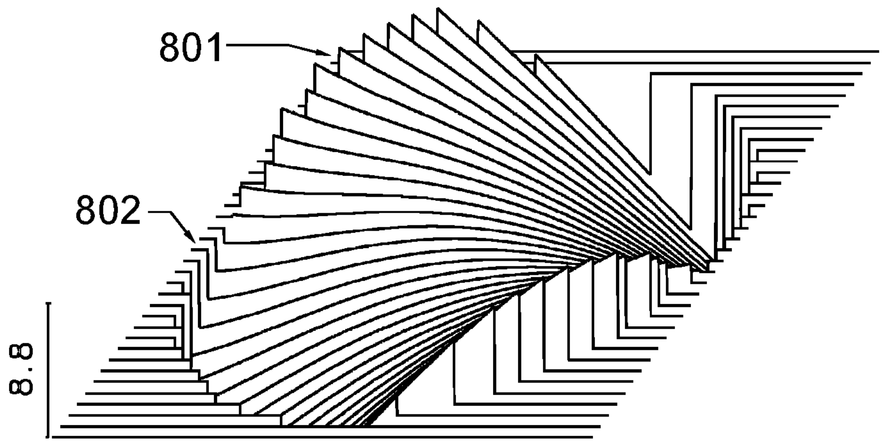
FIG. 8 shows the wavefront error plotted as a contour map for the lens described by Table 3.

A further example showing how the invention can be used to measure the refractive characteristics of the human eye employs the OSLO optical design software, available from Lambda Research Corporation, Littleton, MA 01460, United States. A model is set up with the BW eye from their lens database. There are other models available that more accurately represent the human eye, but this one is very simple and adequate for the following demonstration of computing procedure. The prescription data are shown in Table 3. Surface 1, as specified in the model eye specification, is modified so as to induce a focus error. In addition to the base radius change, the surface is designated at a toric having a curvature in the x direction of 0.12. In addition, the surface is rotated 45 degrees. An entrance pupil is divided into thirteen circular segments shown in FIG. 7, the opening of the pupil (701) confines segments (702) shown. For a 4 mm diameter pupil, each segment diameter is 1 mm. If a larger pupil diameter is desired, such as a 7 mm pupil which might be desired for night vision testing, more segments could be specified. Also, additional segments may be required for measuring optical power of severely deformed optical surfaces. Rays are traced through the deformed lens, and the wavefront error at the exit pupil is calculated, thus providing the pupil function. This value can be used to assess any refractive property of the optical system and serves as an input for producing corrective lenses. The data for the example are shown as optical path difference (OPD) or wavefront error, measured in number of waves at $\lambda$=0.55 nanometers, and as focus errors in diopters of power. The diopters of refractive power range from −3.3 to +1.4. In FIG. 8 the wavefront error is provided as a contour plot, (801) indicating plus wavefront contours, and (802) indicating minus contours. A simple lens, placed in contact with the cornea for the prescription data shown in FIG. 5, can easily correct for the refractive errors shown. The prescription data for the corrective lens is guided by the OPD measurement obtained using pupil segmentation. The lens construction data are given in Table 5 according to the formula used in OSLO to describe a 4th degree surface. If the deformation of the test surface had been greater, a higher degree polynomial may have been required.

Tables

TABLE 1

*LENS DATA Focusing objective

| SRF | RADIUS | THICKNESS | APERTURE RADIUS | GLASS |
|---|---|---|---|---|
| 1 | PUPIL | 16.999994 V | 3.406807 AS | AIR * |
| 2 | −15.295032 V | 1.000000 | 4.200000 | N-LAK33B C |
| 3 | −54.056536 V | 11.999996 V | 4.200000 | AIR |
| 4 | −36.559188 V | 1.999998 V | 5.500000 | N-LAF32 C |
| 5 | −20.366807 V | 3.195163 V | 5.500000 | AIR |
| 6 | 12.030206 V | 3.500000 | 5.600000 | FK51 C |
| 7 | −24.451824 V | 3.981553 V | 5.600000 | AIR |
| 8 | −11.450312 V | 1.200000 | 5.000000 | SF4 C |
| 9 | −33.084830 V | 29.258342 S | 5.000000 | AIR |
| IMAGE | — | — | .700000 S | * |

*MULTI-CONFIGURATION LENS DATA

Group 1 surf 2 to 5 EFL −141.1
Group 2 surf 6 to 9 EFL 34.2

| MAGNIFICATION | CFG1 | CFG2 | CFG3 | CFG4 |
|---|---|---|---|---|
| GRP1 | 1.411e−18 | −22.6852 | −0.6101 | 0.3825 |
| GRP2 | −0.1932 | −0.0101 | −0.1289 | −0.2851 |

| CFG MAG | EFL | IMAGE DISTANCE | EFFECTIVE F/# | INFINITY F/# | IMAGE HEIGHT | FIELD ANGLE |
|---|---|---|---|---|---|---|
| 1 | 27.2545 | 29.2583 | 4.0000 | .7000 | 1.4713 | −2.725e−19 |
| 2 | 26.3283 | 23.0329 | 4.0000 | .6997 | 3.0528 | .2293 |
| 3 | 26.9210 | 27.0661 | 4.0000 | .7000 | 8.8996 | .0787 |
| 4 | 27.7396 | 32.3536 | 4.0000 | .7002 | −6.4186 | −.1091 |

*GROUP AIR SPACES FOR MULTI-CONFIGURATION SYSTEMS

| CFG | OBJ<−>GRP1 | GRP1<−>GRP2 | GRP2<−>IMS |
|---|---|---|---|
| 1 | 1.000e20 | 3.1952 | 29.2583 |
| 2 | −108.0000 | 9.4207 | 23.0329 |
| 3 | −333.0000 | 5.3871 | 27.0661 |
| 4 | 267.0000 | .1000 | 32.3536 |

TABLE 2

| LENS DATA SYMMETRICAL RELAY LENS | | | | |
|---|---|---|---|---|
| SRF | Radius | THICKNESS | APERTURE RADIUS | GLASS |
| OBJ | — | 26.915863 | .750000 | AIR * |
| 1 | 66.340965 V | 2.000000 | 4.500000 | N-LAK33A C |
| 2 | −10.034732 V | .581416 V | 4.500000 | AIR |
| 3 | −8.695806 V | .700000 | 4.500000 | N-KZFS5 C |
| 4 | 11.507622 V | .405999 V | 4.500000 | AIR |
| 5 | 12.111436 V | 2.000000 | 4.500000 | N-LAK33A C |
| 6 | −49.044924 V | 8.000000 | 4.500000 | AIR |
| AST | — | 8.000000 P | 3.568930 AS | AIR |
| 8 | 49.044924 P | 2.000000 P | 4.500000 | N-LAK33A P |
| 9 | −12.111436 P | .405999 P | 4.500000 | AIR |
| 10 | −11.507622 P | .700000 P | 4.500000 | N-KZFS5 P |
| 11 | 8.695806 P | .581416 P | 4.500000 | AIR |
| 12 | 10.034732 P | 2.000000 P | 4.500000 | N-LAK33A P |
| 13 | −66.340965 P | 26.925741 | 4.500000 | AIR |
| IMS | — | — | .746382 | — |

PARAXIAL PROPERTIES

Image num. aperture: 0.125000
Working F-number: 4.000000
Object height: −0.750000
Gaussian image height: 0.745271
Total track length: 80.915855
Paraxial magnification: −0.993694
Effective focal length: 22.171768

TABLE 3

| SRF | RADIUS | THICKNESS | APERTURE RADIUS | GLASS | SPE | NOTE |
|---|---|---|---|---|---|---|
| OBJ | — | 1.000e+20 | 3.4921e+18 | AIR | — | — |
| 1 | 7.500000 | .600000 | 6.000000 | CORN | M | * |
| 2 | 6.400000 | 3.000000 | 5.000000 | AQU | M | * |
| AST | — | — | 1.758160 AS | AQU | M | — |
| 4 | 10.100000 | 4.600000 | 4.000000 | LENS | M | — |
| 5 | −6.100000 | 16.560000 | 4.000000 | VIT | M | — |
| 6 | −12.500000 | 0.050000 | 6.000000 | BK7 | C | — |
| IMS | −12.500000 | — | 6.000000 | — | — | — |

*TILT/DECENTER DATA

| | | | | | | | | |
|---|---|---|---|---|---|---|---|---|
| 1 | DT | 1 | DCX | — | DCY | — | DCZ | — |
| | | | TLA | — | TLB | — | TLC | 45.000000 |
| 2 | DT | 1 | DCX | — | DCY | — | DCZ | — |
| | | | TLA | — | TLB | — | TLC | −45.000000 |

*SURFACE TAG DATA

| | | |
|---|---|---|
| 1 | CVX | .120000 |

*PARAXIAL SETUP OF LENS

APERTURE

ENTRANCE BEAM RADIUS: * 2.000000

FIELD

FIELD ANGLE: * 2.000000
EFFECTIVE FOCAL LENGTH: 25.553545

TABLE 4

| SEGMENT | UNSCALED SEGMENTED PUPIL X | UNSCALED SEGMENTED PUPIL Y | P | 4 mm Pupil OPD | 4 mm Pupil Diopters |
|---|---|---|---|---|---|
| 1 | −1 | 0 | 1 | −2.7 | −1.1 |
| 2 | −0.5 | 0 | 0.5 | −1.1 | −1.1 |
| 3 | 0 | 0 | 0 | — | 0 |

TABLE 4-continued

| SEGMENT | UNSCALED SEGMENTED PUPIL X | UNSCALED SEGMENTED PUPIL Y | P | 4 mm Pupil OPD | 4 mm Pupil Diopters |
|---|---|---|---|---|---|
| 4 | 0.5 | 0 | 0.5 | −1.1 | −1.1 |
| 5 | 1 | 0 | 1 | −2.7 | −1.1 |
| 6 | −0.5 | −0.5 | 0.707 | −6.5 | −3.3 |
| 7 | 0 | −0.5 | 0.5 | −1.1 | −1.1 |
| 8 | .5 | −0.5 | 0.707 | 2.7 | 1.4 |
| 9 | 0 | −1 | 1 | −2.7 | −0.7 |
| 10 | 0 | −0.5 | 0.5 | −1.1 | −1.1 |
| 11 | 0 | 0.5 | 0.5 | −1.1 | −1.1 |
| 12 | 0.5 | 0.5 | 0.707 | −6.5 | −3.3 |
| 13 | — | 1 | 1 | −2.7 | −.7 |

TABLE 5

| SRF | RADIUS | THICKNESS | APERTURE RADIUS | GLASS |
|---|---|---|---|---|
| 1 | 5.341178 V | .500000 | 2.006224 S | ACRYL C ASP |
| 2 | 5.000000 | — | 1.943763 S | — |
| 1 ASP ASX 4 - ASYMMETRIC GENERAL ASPHERE | | | | |
| AS0-AS1 2.2299e−04 AS2 9.1526e−04 AS3 4.4890e−03 AS4 4.7760e−03 AS5 4.4880e−03 AS6 5.7416e−06 AS7 5.7898e−06 AS8 −8.8373e−06 AS9 5.2950e−06 AS10 −8.1497e−05 AS11 4.3865e−05 AS12 −1.5816e−05 AS13 1.9984e−04 AS14 −4.7804e−05 | | | | |

The invention claimed is:

1. A method to diagnose conditions of the eye including a diffusive image surface and sensor, the method comprising: providing an object;

passing light from the object through a relay lens system including an aperture stop imaged into the pupil of the system under test, said aperture stop divided into segments which can be opened individually to accept light from said illuminated object;

passing light from the relay lens system through a focusing objective having at least one movable lens element, whereby the focusing objective lens can achieve focus of the object on the retina for a range of object distances presented to the eye, and thereby forming an image of the object on the retina, light from the retina passing back through the focusing objective lens and forming an image on the object plane of said relay lens system;

placing an image sensor at the image plane of said relay lens for which said object and image are in the same optical path divided by a beam splitter;

controlling the movable lens element for focus determination according to the output from the image sensor;

placing a second beam-splitter in a fixed portion of the focusing objective, creating a second optical path to the eye under test whereby a second illuminated source is imaged onto the eye under test;

programming an object source for multiple wavelengths (colors) of light which can be used to compare the physical responses of a human eye to different stimuli;

and computing the focus information provided by opening individual segments which can be used to determine refractive properties of the pupil under test.

* * * * *